United States Patent
Tachibana et al.

(10) Patent No.: US 10,112,890 B2
(45) Date of Patent: Oct. 30, 2018

(54) COMPOUND, SALT OF COMPOUND, EXTERNAL AGENT FOR SKIN, COSMETIC, AND FOOD ADDITIVE

(71) Applicant: SHOWA DENKO K.K., Tokyo (JP)

(72) Inventors: Toru Tachibana, Mobara (JP); Ryota Niibayashi, Isesaki (JP); Daisuke Yagyu, Funabashi (JP)

(73) Assignee: SHOWA DENKO K.K., Minato-ku, Tokyo (JP)

( * ) Notice: Subject to any disclaimer, the term of this patent is extended or adjusted under 35 U.S.C. 154(b) by 0 days.

(21) Appl. No.: 15/543,261

(22) PCT Filed: Jan. 15, 2016

(86) PCT No.: PCT/JP2016/051113
§ 371 (c)(1),
(2) Date: Jul. 13, 2017

(87) PCT Pub. No.: WO2016/117465
PCT Pub. Date: Jul. 28, 2016

(65) Prior Publication Data
US 2017/0369425 A1  Dec. 28, 2017

(30) Foreign Application Priority Data
Jan. 19, 2015 (JP) .................... 2015-007865

(51) Int. Cl.
C07C 235/12 (2006.01)
A23L 33/15 (2016.01)
A61K 8/67 (2006.01)
A61Q 19/00 (2006.01)

(52) U.S. Cl.
CPC ......... *C07C 235/12* (2013.01); *A23L 33/15* (2016.08); *A61K 8/673* (2013.01); *A61Q 19/00* (2013.01); *A23V 2002/00* (2013.01); *A61K 2800/10* (2013.01)

(58) Field of Classification Search
CPC ......... A23L 33/15; A61K 31/197; A61K 8/44; A61Q 19/00; C07C 235/12; A23V 2002/00
See application file for complete search history.

(56) References Cited

U.S. PATENT DOCUMENTS

| | | | |
|---|---|---|---|
| 2,519,462 A | 8/1950 | Harris et al. | |
| 2,557,284 A | 6/1951 | Harris et al. | |
| 3,376,334 A | 4/1968 | Kobayashi et al. | |

FOREIGN PATENT DOCUMENTS

| JP | 60-136589 A | 7/1985 |
| JP | 06-305940 A | 11/1994 |
| WO | 2014/080307 A2 | 5/2014 |
| WO | 2014/195810 A2 | 12/2014 |
| WO | 2014/195961 A1 | 12/2014 |
| WO | WO2014/195810 | * 12/2014 |

OTHER PUBLICATIONS

Tonio Wiederholt et al., "Calcium pantothenate modulates gene expression in proliferating human dermal fibroblasts", Experimental Dermatology, 2009, pp. 969-978, 18.
Bernd J. Weimann et al., "Studies on Wound Healing: Effects of Calcium D-Pantothenate on the Migration, Proliferation and Protein Synthesis of Human Dermal Fibroblasts in Culture", Int. J. Vitam. Nutr. Res., 1999, pp. 113-119, 69 (2).
Taketami Sakuragi et al., "The Synthesis of Long Chain Fatty Acid Derivatives of Pantothenic Acid1", Journal of the American Chemical Society, 1956, pp. 838-839, vol. 7.
International Search Report for PCT/JP2016/051113, dated Mar. 15, 2016.
Taketami Sakuragi et al., "The Biological Utilization of the Palmitic Acid Esters of Pantothenic Acid", The Journal of Nutrition, American Society for Nutrition, US, vol. 59, No. 3, Jul. 10, 1956 (Jul. 10, 1956), pp. 327-336 (10 pages total).
Extended European Search Report dated Jul. 5, 2018 issued by the European Patent Office in counterpart application No. 16740072.0.

* cited by examiner

*Primary Examiner* — Pancham Bakshi
*Assistant Examiner* — Mark R Luderer
(74) *Attorney, Agent, or Firm* — Sughrue Mion, PLLC

(57) ABSTRACT

Provided is a compound represented by Formula (1) or a salt thereof (in the formula, $R^1$ and $R^2$ each independently represent a hydrogen atom or a linear or branched acyl group having 11 to 30 carbon atoms, a hydrocarbon group bonded to a carbonyl carbon of the acyl group is a saturated or unsaturated hydrocarbon group, and at least one of $R^1$ and $R^2$ represents the acyl group).

(1)

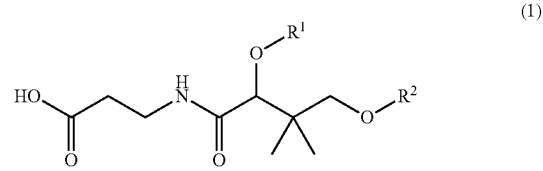

12 Claims, No Drawings

COMPOUND, SALT OF COMPOUND, EXTERNAL AGENT FOR SKIN, COSMETIC, AND FOOD ADDITIVE

TECHNICAL FIELD

The present invention relates to a compound, a salt of the compound, an external agent for skin, a cosmetic, and a food additive.

Priority is claimed on Japanese Patent Application No. 2015-007865, filed on Jan. 19, 2015, the content of which is incorporated herein by reference.

BACKGROUND ART

Pantothenic acid is also referred to as vitamin B5, is a constituent factor of coenzyme A which is indispensable for metabolism of carbohydrates, lipids, and proteins and production of energy, and is also involved in synthesis of cholesterol, hormones, and immune antibodies.

As described above, pantothenic acid is an important compound which is involved in various functions in a living body and various symptoms appear in the body when pantothenic acid is deficient. For example, secretion of sebum is disturbed and turnover of the skin is not properly performed due to deficiency of pantothenic acid, and dermatitis, acne, and rough skin are caused. Further, it is also known that white hair or alopecia is caused when pantothenic acid is deficient (see PTL 1).

In addition, pantothenic acid is known to be involved in production of collagen precursors or growth factors of epidermal cells (see NPL 1) and it has also been reported that pantothenic acid has a fibroblast proliferative action (see NPL 2).

Since various symptoms are caused due to deficiency of pantothenic acid, various external agents formed by blending pantothenic acid, pantothenic acid derivatives, or salts of these have been examined in order to ameliorate these symptoms.

However, the above-described external agents of the related art formed by blending pantothenic acid and the like have a problem that the effect of ameliorating symptoms is insufficient. In order to ameliorate symptoms caused by the deficiency of pantothenic acid, pantothenic acid derivatives having high absorbability into a body are considered to be effective for use. Therefore, a novel pantothenic acid derivative having high absorbability into a body has been needed.

CITATION LIST

Patent Literature

[PTL 1] Japanese Unexamined Patent Application, First Publication No. H06-305940

Non-Patent Literature

[NPL 1] Exp Dermatol; 18 (11) 969-78, 2009
[NPL 2] Int J Vitam Nutr Res; 69 (2) 113-9, 1999

SUMMARY OF INVENTION

Technical Problem

An object of the present invention is to provide a novel pantothenic acid derivative having high absorbability into a body.

Solution to Problem

According to the present invention, there is provided a compound represented by Formula (1) or a salt thereof.

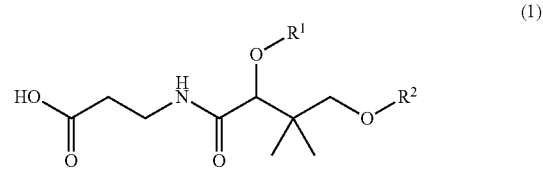

(In the formula, $R^1$ and $R^2$ each independently represent a hydrogen atom or a linear or branched acyl group having 11 to 30 carbon atoms, a hydrocarbon group bonded to a carbonyl carbon of the acyl group is a saturated or unsaturated hydrocarbon group, and at least one of $R^1$ and $R^2$ represents the acyl group.)

In the compound or a salt thereof of the present invention, the compound represented by Formula (1) may be a compound represented by Formula (1)-3.

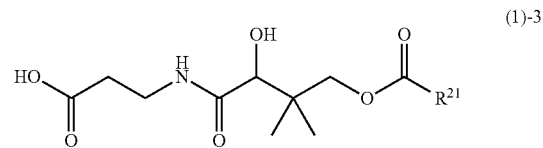

(In the formula, $R^{21}$ represents a linear or branched saturated or unsaturated hydrocarbon group having 10 to 29 carbon atoms.)

In the compound or a salt thereof of the present invention, $R^1$ and $R^2$ may each independently represent a hydrogen atom or a linear or branched acyl group having 14 to 20 carbon atoms.

In the compound or a salt thereof of the present invention, $R^{21}$ may represent a linear or branched saturated or unsaturated hydrocarbon group having 15 to 17 carbon atoms.

In the compound or a salt thereof of the present invention, the compound represented by Formula (1) may be a compound represented by Formula (1)-301 or (1)-302.

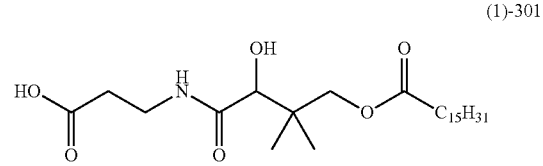

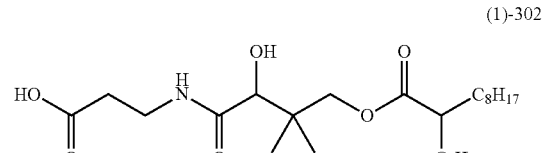

The salt of the compound of the present invention may be a salt formed by the compound becoming a cation together with an inorganic anion or an organic anion, or a salt formed by the compound becoming an anion together with an inorganic cation or an organic cation.

The salt of the compound of the present invention may be a salt formed by the compound becoming a cation together with one or more anions selected from the group consisting of a hydroxide ion, a nitrate ion, a sulfate ion, a carbonate ion, a bicarbonate ion, a halide ion, a formate ion, an acetate ion, a citrate ion, a tartrate ion, an oxalate ion, a fumarate ion, anions of saturated or unsaturated chain fatty acid having 3 to 20 carbon atoms, anions of carnitine and derivatives thereof, anions of hydroxy citric acid and derivatives thereof, anions of ascorbic acid, and anions of ascorbyl phosphoric acid and derivatives thereof.

The salt of the compound of the present invention may be a salt formed by the compound becoming an anion together with one or more cations selected from the group consisting of a sodium ion, a potassium ion, a calcium ion, a magnesium ion, a zinc ion, an ammonium ion, carnitine, and cations of carnitine derivatives.

Further, according to the present invention, there is provided an external agent for skin containing: the compound or a salt thereof.

Further, according to the present invention, there is provided a cosmetic containing: the external agent for skin.

Further, according to the present invention, there is provided a food additive containing: the compound or a salt thereof.

Advantageous Effects of Invention

The compound or a salt thereof of the present invention has high absorbability into a body.

DESCRIPTION OF EMBODIMENTS

<Compound and Salt of Compound>

A compound according to the present invention is represented by Formula (1) (hereinafter, also simply referred to as a "compound (1)"). Further, a salt of the compound according to the present invention is a salt of the compound (compound (1)) represented by Formula (1).

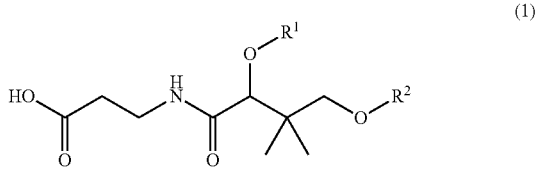

(1)

(In the formula, $R^1$ and $R^2$ each independently represent a hydrogen atom or a linear or branched acyl group having 11 to 30 carbon atoms, a hydrocarbon group bonded to a carbonyl carbon of the acyl group is a saturated or unsaturated hydrocarbon group, and at least one of $R^1$ and $R^2$ represents the acyl group.)

The compound (1) and a salt thereof (hereinafter, these compounds are also simply collectively referred to as the "compound (1) and the like") are derivatives of pantothenic acid and have higher absorbability into a body such as skin permeability than pantothenic acid, pantothenic acid derivatives, and salts of these of the related art. This is because the compound (1) and the like are amphiphilic, having a lipid-soluble portion in addition to a water-soluble portion since they contain an acyl group having 11 to 30 carbon atoms. Further, the compound (1) and the like are absorbed into a body and then decomposed by a biological enzymatic reaction, thereby obtaining pantothenic acid. Therefore, when the compound (1) and the like are used, a sufficient amount of pantothenic acid can be allowed to reach skin tissues. For example, an external agent for skin containing the compound (1) and the like is useful as a sebum control agent, a normalizing agent for skin turnover, an anti-inflammatory agent, an anti-acne agent, a skin roughness-preventing agent, a hair whitening-preventing agent, an external agent for hair growth, and an anti-aging agent.

Moreover, a "derivative" in the present specification means that one or more hydrogen atoms of an original compound are substituted with a group (substituent) other than a hydrogen atom.

In the formula, $R^1$ and $R^2$ each independently represent a hydrogen atom or a linear or branched acyl group having 11 to 30 carbon atoms and a hydrocarbon group (hydrocarbyl group) bonded to a carbonyl carbon of the acyl group is a saturated or unsaturated hydrocarbon group. In the acyl group, the saturated or unsaturated hydrocarbon group has 10 to 29 carbon atoms.

In the acyl group, the saturated hydrocarbon group (alkyl group) bonded to a carbonyl carbon (a carbon atom constituting a carbonyl group) has 10 to 29 carbon atoms and may be linear or branched.

Specific examples of the alkyl group include linear alkyl groups having 10 to 29 carbon atoms such as a decyl group, an undecyl group, a dodecyl group, a tridecyl group, a tetradecyl group, a pentadecyl group, a hexadecyl group, a heptadecyl group, an octadecyl group, a nonadecyl group, an icosyl group, a henicosyl group, a docosyl group, a tricosyl group, a tetracosyl group, a pentacosyl group, a hexacosyl group, a heptacosyl group, an octacosyl group, and a nonacosyl group.

Further, specific examples of the alkyl group include branched alkyl groups having the same number of carbon atoms as the carbon atoms of the linear alkyl groups, such as a hexylnonyl group.

In the acyl group, the unsaturated hydrocarbon group bonded to a carbonyl carbon has 10 to 29 carbon atoms and may be linear or branched.

As the unsaturated hydrocarbon group, a group formed by one or more single bonds (C—C) between carbon atoms in the alkyl group being substituted with a double bond (C═C) or a triple bond (C≡C) which is an unsaturated bond may be exemplified.

In the unsaturated hydrocarbon group, the number of unsaturated bonds may be only one or two or more. In a case where the number of unsaturated bonds is two or more, these unsaturated bonds may be formed of only double bonds or only triple bonds or may have double bonds and triple bonds in a mixed state.

The position of the unsaturated bond in the unsaturated hydrocarbon group is not particularly limited.

In the unsaturated hydrocarbon group, the number of unsaturated bonds is preferably in a range of 1 to 3 and more preferably 1 or 2.

Further, it is preferable that the unsaturated hydrocarbon group has only double bonds as unsaturated bonds.

Particularly preferred examples of the unsaturated hydrocarbon group include linear alkenyl groups having 10 to 29 carbon atoms such as a decenyl group, an undecenyl group, a dodecenyl group, a tridecenyl group, a tetradecenyl group, a pentadecenyl group, a hexadecenyl group, a heptadecenyl group, an octadecenyl group, a nonadecenyl group, an icosenyl group, a henicosenyl group, a docosenyl group, a tricosenyl group, a tetracosenyl group, a pentacosenyl group, a hexacosenyl group, a heptacosenyl group, an octacosenyl group, and a nonacosenyl group.

Further, particularly preferred examples of the unsaturated hydrocarbon group include branched alkenyl groups having the same number of carbon atoms as the carbon atoms of the linear alkenyl groups.

The number of carbon atoms of the acyl group as $R^1$ and $R^2$ is preferably in a range of 11 to 25, more preferably in a range of 11 to 20, still more preferably in a range of 14 to 20, and particularly preferably in a range of 16 to 18. In other words, the number of carbon atoms of the hydrocarbon group bonded to a carbonyl carbon of the acyl group is preferably in a range of 10 to 24, more preferably in a range of 10 to 19, still more preferably in a range of 13 to 19, and particularly preferably in a range of 15 to 17.

It is preferable that the hydrocarbon group bonded to a carbonyl carbon of the acyl group is an alkyl group or an alkenyl group.

Here, in the formula, at least one of $R^1$ and $R^2$ represents the acyl group. In other words, examples of the compound (1) include a compound represented by Formula (1)-1 in which both of $R^1$ and $R^2$ represent the acyl group (hereinafter, also simply referred to as a "compound (1)-1"), a compound represented by Formula (1)-2 in which $R^1$ represents the acyl group and $R^2$ represents a hydrogen atom (hereinafter, also simply referred to as a "compound (1)-2"), and a compound represented by Formula (1)-3 in which $R^1$ represents a hydrogen atom and $R^2$ represents the acyl group (hereinafter, also simply referred to as a "compound (1)-3").

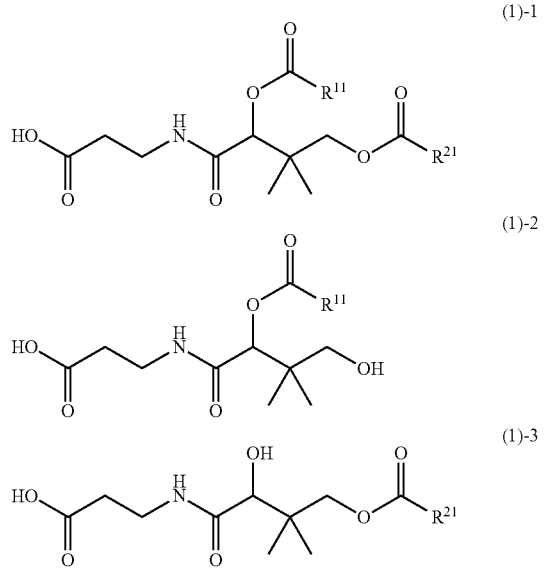

(In the formula, $R^{11}$ and $R^{21}$ each independently represent a linear or branched saturated or unsaturated hydrocarbon group having 10 to 29 carbon atoms.)

In the formula, $R^{11}$ and $R^{21}$ each independently represent a linear or branched saturated or unsaturated hydrocarbon group (hydrocarbyl group) having 10 to 29 carbon atoms, and this hydrocarbon group is the same as the hydrocarbon group bonded to a carbonyl carbon of the acyl group as $R^1$ and $R^2$ above.

For example, the number of carbon atoms of $R^{11}$ and $R^{21}$ is preferably in a range of 10 to 24, more preferably in a range of 10 to 19, still more preferably in a range of 13 to 19, and particularly preferably in a range of 15 to 17.

The salt of the compound (1) may be a salt formed from two or more molecules which are molecules derived from the compound (1) and other molecules or may be an internal salt formed from one molecule derived from the compound (1).

Among examples of the salt of the compound (1), the above-described salt formed from two or more molecules is not particularly limited as long as the structure thereof is formed by the compound (1) reacting with an acid or a base to form a salt. Such a salt may be any of a salt formed by the compound (1) becoming a cation together with an anion (an inorganic anion or an organic anion) and a salt formed by the compound (1) becoming an anion together with a cation (an inorganic cation or an organic cation).

As the portion (group) of the compound (1) which may become a cationic moiety, a group represented by Formula "—NH—" may be exemplified. As the salt of the compound (1), a salt formed by the group of the compound (1) which is represented by Formula "—NH—" becoming a monovalent cationic moiety together with an anion may be exemplified. Here, as the cationic moiety, a part ($—NH_2^+—$) obtained by coordinating a hydrogen ion ($H^+$) with a nitrogen atom of the group represented by Formula "—NH—" may be exemplified. The valence of the anion in this case is not particularly limited and may be one (monovalent) or two (divalent) or greater. In a case where the anion is monovalent, the number of anions forming the salt of the compound (1) and the number of cations derived from the compound (1) are both one. Further, in a case where the anion is n-valent (n represents an integer of 2 or greater), the number of anions forming the salt of the compound (1) is typically one and the number of cations derived from the compound (1) is n or less and preferably n. In this case, all of the plurality of cations may be the same as or different from each other or some of the plurality of cations may be the same as each other.

In addition, as the portion (group) of the compound (1) which may become an anionic moiety, a carboxy group (—C(=O)—OH) may be exemplified. As the salt of the compound (1), a salt formed from a cation and an anionic moiety obtained by the carboxy group of the compound (1) becoming an anion (—C(=O)—O$^-$) may be exemplified. The valence of the cation in this case is not particularly limited and may be one (monovalent) or two (divalent) or greater. In a case where the cation is monovalent, the number of cations forming the salt of the compound (1) and the number of anions derived from the compound (1) are both one. Further, in a case where the cation is m-valent (m represents an integer of 2 or greater), the number of cations forming the salt of the compound (1) is typically one and the number of anions derived from the compound (1) is m or less and preferably m.

As described above, the numbers of cations and anions constituting the salt in one molecule of the compound (I) may be respectively only one or two or greater. In a case where the numbers of cations and anions are both two or greater, all of these cations or anions may be the same as or different from each other or some of these cations or anions may be the same as each other.

In this case, it is preferable that the salt of the compound (1) is electrically neutral as the whole molecule, in other words, the total value of the valence of cations in one molecule of the compound (1) and the total value of the valence of anions in one molecule of the compound (1) are the same as each other.

The anion that forms the salt of the compound (1) together with the compound (1) as a cation is not particularly limited.

Among examples of the anion, preferred examples of the inorganic anion include a hydroxide ion, a nitrate ion, a sulfate ion, a carbonate ion, a bicarbonate ion, and a halide ion. Further, examples of the halide ion include a fluoride ion, a chloride ion, a bromide ion, and an iodide ion.

Among examples of the anion, preferred examples of the organic anion include anions of carboxylic acid, anions of carnitine and derivatives thereof, anions of hydroxy citric acid and derivatives thereof, anions of ascorbic acid, and anions of ascorbyl phosphoric acid and derivatives thereof.

The anion of the carboxylic acid may be an anion of monocarboxylic acid (monovalent carboxylic acid) or an anion of polyvalent carboxylic acid such as dicarboxylic acid or tricarboxylic acid.

Examples of the anion of the carboxylic acid include a formate ion; an acetate ion; an anion of saturated or unsaturated chain fatty acid having 3 or more carbon atoms such as a propanoate (propionate) ion, a butanoate (butyrate) ion, a pentanoate (valerate) ion, a hexanoate (caproate) ion, a heptanoate (enanthate) ion, an octanoate (caprylate) ion, a nonanoate (pelargonate) ion, a decanoate (caprate) ion, a dodecanoate (laurate) ion, a tetradecanoate (myristate) ion, a pentadecanoate ion, a hexadecanoate (palmitate) ion, a heptadecanoate ion, an octadecanoate (stearate) ion, an eicosanoate (arachidate) ion, a cis-9-octadecenoate (oleate) ion, a cis,cis-9,12-octadecadienoate (linoleate) ion, a cis,cis,cis-9,12,15-octadecatrienoate (α-linolenate) ion, an all-cis-6,9,12-octadecatrienoate (γ-linolenate) ion, or a (5Z,8Z,11Z,14Z)-icosa-5,8,11,14-tetraenoate (arachidonate) ion; an anion of saturated or unsaturated dicarboxylic acid having 2 or more carbon atoms such as an oxalate ion, a malonate ion, a succinate ion, a glutarate ion, an adipate ion, a fumarate ion, or a maleate ion; and an anion of hydroxy acid such as a citrate ion, a tartrate ion, or a hydroxy citrate ion.

Further, the "fatty acid" in the present specification indicates a monocarboxylic acid having a chain structure unless otherwise noted.

The number of carbon atoms of the above-described anion of saturated or unsaturated chain fatty acid having 3 or more carbon atoms is preferably in a range of 3 to 25 and more preferably in a range of 3 to 20. Further, it is preferable that the anion of unsaturated chain fatty acid having 3 or more carbon atoms has 1 to 4 unsaturated bonds (double bonds between carbon atoms).

The number of carbon atoms of the above-described anion of saturated or unsaturated dicarboxylic acid having 2 or more carbon atoms is preferably in a range of 2 to 6 and more preferably in a range of 2 to 4. Further, it is preferable that the anion of unsaturated dicarboxylic acid having 2 or more carbon atoms has one unsaturated bond (double bond between carbon atoms).

In the anion of saturated or unsaturated chain fatty acid having 3 or more carbon atoms and the anion of saturated or unsaturated dicarboxylic acid having 2 or more carbon atoms, it is advantageous that the number of carbon atoms is in the above-described numerical value range and the number of unsaturated bonds is in the above-described numerical value range from the viewpoints that the raw ingredients are easily obtained and the production is easily performed.

It is preferable that the anion that forms the salt of the compound (1) together with the compound (1) as a cation is one or more anions selected from the group consisting of a hydroxide ion, a nitrate ion, a sulfate ion, a carbonate ion, a bicarbonate ion, a halide ion, a formate ion, an acetate ion, a citrate ion, a tartrate ion, an oxalate ion, a fumarate ion, anions of saturated or unsaturated chain fatty acid having 3 to 20 carbon atoms, anions of carnitine and derivatives thereof, anions of hydroxy citric acid and derivatives thereof, anions of ascorbic acid, and anions of ascorbyl phosphoric acid and derivatives thereof.

The cation that forms the salt of the compound (1) together with the compound (1) as an anion is not particularly limited.

Among examples of the cation, preferred examples of the inorganic cation include a sodium ion, a potassium ion, a calcium ion, a magnesium ion, a lithium ion, a barium ion, an aluminum ion, a zinc ion, a copper ion ($Cu^{30}$, $Cu^{2+}$), an iron ion ($Fe^{2+}$, $Fe^{3+}$), a manganese ion, a nickel ion, a tin ion ($Sn^{2+}$, $Sn^{4+}$), and an ammonium ion.

Among examples of the cation, preferred examples of the organic cation include carnitine and cations of carnitine derivatives.

It is preferable that the cation that forms the salt of the compound (1) together with the compound (1) as an anion is one or more cations selected from the group consisting of a sodium ion, a potassium ion, a calcium ion, a magnesium ion, a zinc ion, an ammonium ion, carnitine, and cations of carnitine derivatives.

Among examples of the salt of the compound (1), the internal salt means that a carboxy group (—C(=O)=—OH) in the compound (1) is dissociated and becomes an anionic moiety (—C(=O)—O⁻), a proton is added to a group represented by Formula "—NH—", and a cationic moiety represented by Formula "—NH$_2^+$" is obtained.

As a preferred example of the salt of the compound (1), a salt formed by the compound (1) becoming a cation together with one or more anions selected from the group consisting of a hydroxide ion, a nitrate ion, a sulfate ion, a carbonate ion, a bicarbonate ion, a halide ion, a formate ion, an acetate ion, a citrate ion, a tartrate ion, an oxalate ion, a fumarate ion, anions of saturated or unsaturated chain fatty acid having 3 to 20 carbon atoms, anions of carnitine and derivatives thereof, anions of hydroxy citric acid and derivatives thereof, anions of ascorbic acid, and anions of ascorbyl phosphoric acid and derivatives thereof may be exemplified.

Further, as a preferred example of the salt of the compound (1), a salt formed by the compound (1) becoming an anion together with one or more cations selected from the group consisting of a sodium ion, a potassium ion, a calcium ion, a magnesium ion, a zinc ion, an ammonium ion, carnitine, and cations of carnitine derivatives may be exemplified.

The compound (1), containing asymmetric atoms in a molecule, has a plurality of stereoisomers. That is, the compound (1) and a salt thereof (the compound (1) and the like) according to the present invention include all these stereoisomers.

The compound (1) and a salt thereof are novel compounds. The compound (1) and a salt thereof have moderate lipid solubility since the number of carbon atoms of the acyl group is 11 or more. Therefore, in a case where the compound (1) and a salt thereof are used as components of an external agent described below, the amount of pantothenic acid reaching the skin tissues is remarkably larger compared to pantothenic acid, pantothenic acid derivatives, and salts of these (for example, salts formed from a carboxy group) of the related art. When compared with a compound in which at least one of $R^{11}$ and $R^{21}$ in Formula (1)-1 represents a saturated or unsaturated hydrocarbon group having 1 to 9 carbon atoms, a compound in which $R^{11}$ and $R^{21}$ in Formula (1)-2 or (1)-3 represent a saturated or unsaturated hydrocarbon group having 1 to 9 carbon atoms, or salts of these compounds, the compound (1) and a salt thereof are the same in that they are acylated substances of a hydroxyl group, but the amount of pantothenic acid reaching the skin tissues is remarkably larger in a case of being used as the components of the external agent described below. Accordingly, the compound (1) and a salt thereof are excellently effective in ameliorating symptoms caused by the deficiency of pantothenic acid.

The compound (1) and a salt thereof are useful as active components of external agents for skin and cosmetics and also useful as active components of food additives because the compound (1) and a salt thereof have high absorbability into a body.

The compound (1) and a salt thereof have moderate water solubility since the number of carbon atoms of the acyl group is 30 or less (the number of carbon atoms of the hydrocarbon group in the acyl group is 29 or less). Therefore, the compound (1) and a salt thereof are easily blended into the external agent described below and have excellent handleability in a case where the compound (1) and a salt thereof are used as components of the external agent, compared to a compound in which at least one of $R^{11}$ and $R^{21}$ in Formula (1)-1 represents a saturated or unsaturated hydrocarbon group having 30 or more carbon atoms, a compound in which $R^{11}$ and $R^{21}$ in Formula (1)-2 or (1)-3 represent a saturated or unsaturated hydrocarbon group having 30 or more carbon atoms, or salts of these compounds.

<Method of Producing Compound (1)>

For example, the compound (1) can be produced using either of two methods, which are method 1 and method 2 described below.

The method 1 is a production method including a process (hereinafter, also simply referred to as a "process of producing a compound ($1^0$)") of reacting a compound represented by Formula (1a) (hereinafter, also simply referred to as a "compound (1a)") with a compound represented by Formula ($1b^1$) (hereinafter, also simply referred to as a "compound ($1b^1$)") to obtain one or more compounds selected from the group consisting of a compound represented by Formula ($1^{o1}$)-1 (hereinafter, also simply referred to as a "compound ($1^{o1}$)-1"), a compound represented by Formula ($1^{o1}$)-2 (hereinafter, also simply referred to as a "compound ($1^{o1}$)-2"), and a compound represented by Formula ($1^{o1}$)-3 (hereinafter, also simply referred to as a "compound ($1^{o1}$)-3"). Hereinafter, in the present specification, the compound ($1^{o1}$)-1, the compound ($1^{o1}$)-2, and the compound ($1^{o1}$)-3 are collectively referred to as the "compound ($1^o$)".

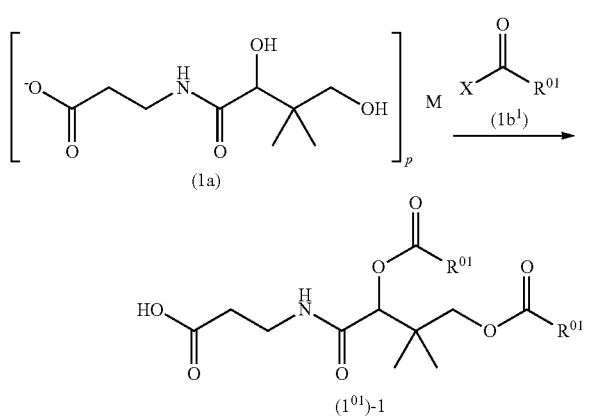

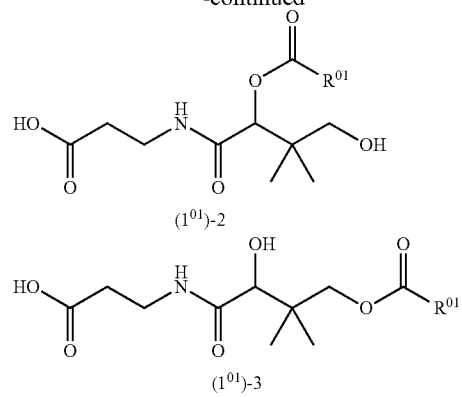

(In the formula, $R^{o1}$ represents a linear or branched saturated or unsaturated hydrocarbon group having 10 to 29 carbon atoms, X represents a leaving group, M represents a cation whose valence is p, and p represents an integer of 1 or greater.)

The method 1 is a method of using only one compound as the compound reacting with the compound (1a).

Among the compounds which can be obtained using the method 1, the compound ($1^{o1}$)-1 corresponds to a compound in which $R^{11}$ and $R^{21}$ are the same as each other among the compounds (1)-1. Further, the compound ($1^{o1}$)-2 corresponds to the compound (1)-2 and the compound ($1^{o1}$)-3 corresponds to the compound (1)-3.

The method 2 is different from the method 1 in terms that a compound represented by Formula ($1^{b2}$) (hereinafter, also simply referred to as a "compound ($1^{b2}$)") is used in addition to the compound ($1^{b1}$) as the compound reacting with the compound (1a). The method 2 is the same as the method 1 except for the point described above, and compounds which can be obtained using the method 2 include a compound represented by Formula ($1^{o2}$)-1 (hereinafter, also simply referred to as a "compound ($1^{o2}$)-1"), a compound represented by Formula ($1^{o2}$)-2 (hereinafter, also simply referred to as a "compound ($1^{o2}$)-2"), a compound represented by Formula ($1^{o2}$)-3 (hereinafter, also simply referred to as a "compound ($1^{o2}$)-3"), a compound represented by Formula ($1^{o3}$)-1 (hereinafter, also simply referred to as a "compound ($1^{o3}$)-1"), and a compound represented by Formula ($1^{o3}$)-2 (hereinafter, also simply referred to as a "compound ($1^{o3}$)-2") in addition to the compound ($1^{o1}$)-1, the compound ($1^{o1}$)-2, and the compound ($1^{o1}$)-3.

In other words, the method 2 is a production method including a process (hereinafter, also simply referred to as the "process of producing the compound ($1^o$)") similar to the case of the method 1) of reacting the compound (1a) with any one or both of the compound ($1b^1$) and the compound ($1b^2$) to obtain one or more compounds selected from the group consisting of the compound ($1^{o1}$)-1, the compound ($1^{o1}$)-2, the compound ($1^{o1}$)-3, the compound ($1^{o2}$)-1, the compound ($1^{o2}$)-2, the compound ($1^{o2}$)-3, the compound ($1^{o3}$)-1, and the compound ($1^{o3}$)-2. Hereinafter, in the present specification, similar to the case of the compound ($1^{o1}$)-1, the compound ($1^{o1}$)-2, and the compound ($1^{o1}$)-3, the compound ($1^{o2}$)-1, the compound ($1^{o2}$)-2, the compound ($1^{o2}$)-3, the compound ($1^{o3}$)-1, and the compound ($1^{o3}$)-2 are collectively referred to as the "compound ($1^o$)". Further, the compound ($1b^1$) and the compound ($1b^2$) are collectively referred to as the "compound (1b)".

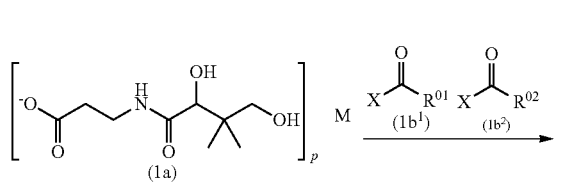

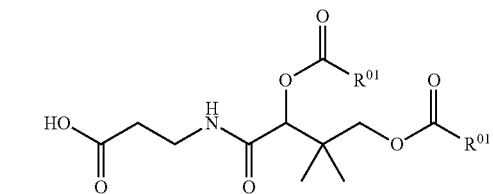
($1^{01}$)-1

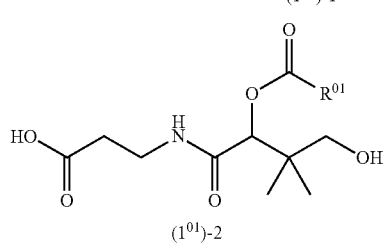
($1^{01}$)-2

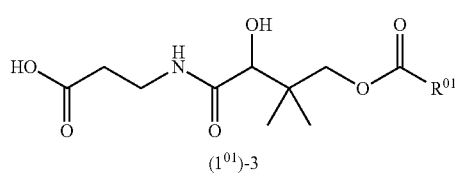
($1^{01}$)-3

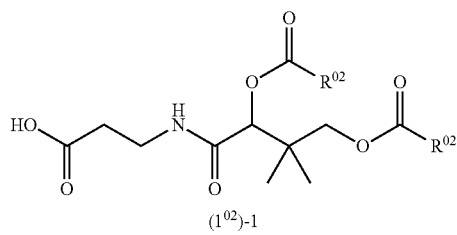
($1^{02}$)-1

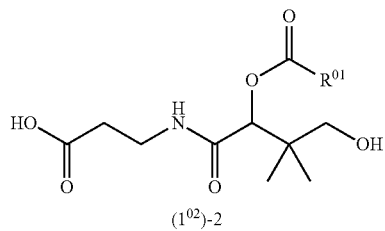
($1^{02}$)-2

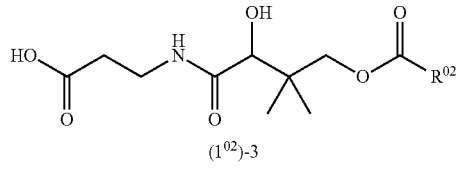
($1^{02}$)-3

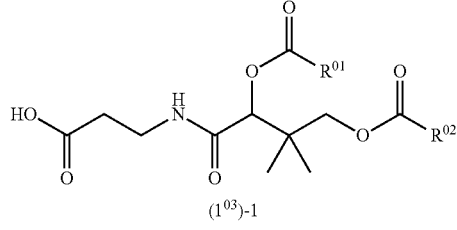
($1^{03}$)-1

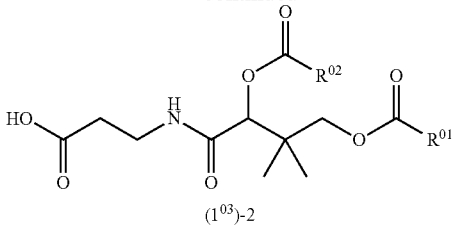
($1^{03}$)-2

(In the formula, $R^{02}$ represents a linear or branched saturated or unsaturated hydrocarbon group having 10 to 29 carbon atoms, different from $R^{01}$; $R^{01}$, X, M, and p have the same definitions as those described above.)

$R^{01}$ and $R^{02}$ are different from each other, and the method 2 is a method of using two kinds of compounds reacting with the compound (1a).

Among the compounds which can be obtained using the method 2, the compound ($1^{01}$)-1 and the compound ($1^{02}$)-1 correspond to compounds in which $R^{11}$ and $R^{21}$ are the same as each other in the compounds (1)-1. Further, the compound ($1^{03}$)-1 and the compound ($1^{03}$)-2 correspond to compounds in which $R^{11}$ and $R^{21}$ are different from each other in the compounds (1)-1. In addition, the compound ($1^{01}$)-2 and the compound ($1^{02}$)-2 correspond to the compound (1)-2 and the compound ($1^{01}$)-3 and the compound ($1^{02}$)-3 correspond to the compound (1)-3.

As described above, the compound ($1^{\circ}$) and the compound (1) are the same as each other. However, for the sake of convenience, the compound ($1^{\circ}$) and the compound (1) are separately noted here.

The method 1 and the method 2 are the same as each other except for the number of compounds to react with the compound (1a). Hereinafter, the description will be made in more detail.

During the process of producing the compound ($1^{\circ}$) according to the method 1 and the method 2, a reaction between the compound (1a) and the compound (1b), that is, an acylation reaction of a hydroxyl group is performed.

The compound (1a) is obtained by forming a salt using a carboxylate anion together with M as a cation.

In the formula, M represents a cation whose valence is p and p represents an integer of 1 or greater.

Examples of the cation as M are the same as those exemplified as the cation that forms a salt together with the compound (1) as an anion. Among these, inorganic cations are preferable.

It is preferable that p represents 1 or 2.

The compounds (1b) (the compound ($1b^1$) and the compound ($1b^2$)) are acylating agents.

In the formulae, $R^{01}$ and $R^{02}$ represent a linear or branched saturated or unsaturated hydrocarbon group having 10 to 29 carbon atoms and have the same definitions as those for $R^{11}$ and $R^{21}$ in Formulae (1)-1 to (1)-3. Here, $R^{01}$ and $R^{02}$ are different from each other.

Further, in the formula, X represents a leaving group. As the leaving group, known ones may be used, and preferred examples thereof include a halogen atom such as a chlorine atom or a bromine atom; an alkoxy group such as a methoxy group; and an alkylcarbonyloxy group such as a methylcarbonyloxy group. In the compound ($1b^1$) and the compound ($1b^2$), X's may be the same as or different from each other.

The amount of the compound (1b) to be used (in the case of the method 2, the total amount of the compound ($1b^1$) and the compound ($1b^2$) to be used) is not particularly limited, and it is preferable that the amount thereof is adjusted as appropriate depending on the type of the target compound ($1^\circ$) as described below. Further, in the case of the method 2, the ratio between the amount of the compound ($1b^1$) to be used and the amount of the compound ($1b^2$) to be used may be adjusted as appropriate depending on the type of the target compound ($1^\circ$).

In the reaction during the process of producing the compound ($1^\circ$) according to the method 1 and the method 2, the compound (1a) may be used alone or in combination of two or more kinds thereof. In a case where two or more kinds thereof are used in combination, the combination and the ratio between the compounds can be arbitrarily selected.

In the present process, regardless of the number of types of the compounds (1a), the combination of the compounds ($1^\circ$) to be obtained is usually the same. Therefore, it is usually sufficient to use only one type of compound (1a). Here, as described below, in a case where the compound ($1^\circ$) is extracted as salts thereof after the present process, the combination of salts of the compound ($1^\circ$) to be obtained may vary depending on the number of types of the compounds (1a).

Here, the case where two types of the compounds (1b) (the compound ($1b^1$) and the compound ($1b^2$)) are used in combination has been described as the method 2, but three or more types of the compounds (1b) may be used in combination as necessary.

It is preferable that the reaction during the process of producing the compound ($1^\circ$) according to the method 1 and the method 2 is performed using a solvent.

The solvent is not particularly limited as long as the solvent does not disturb the reaction, and examples thereof include tetrahydrofuran (THF), 1,4-dioxane, and ether (compound having an ether bond) such as diethyl ether or dibutyl ether.

The solvent may be used alone or in combination of two or more kinds thereof as a mixed solvent. In a case where two or more kinds thereof are used in combination, the combination and the ratio between the solvents can be selected as appropriate depending on the purpose thereof.

The amount of the solvent to be used is not particularly limited and may be selected as appropriate in consideration of the solubility of raw ingredients to be used and stirring properties of a reaction solution. For example, the amount of the solvent to be used can be set such that the concentration of the compound (1a) at the time of starting the reaction is adjusted to be in a range of 10 to 200 mM.

It is preferable that the reaction during the process of producing the compound ($1^\circ$) according to the method 1 and the method 2 is performed using a base.

The base may be any of an inorganic base or an organic base and can be selected as appropriate depending on the purpose thereof, but it is preferable that the base is an organic base.

Examples of the inorganic base include lithium hydroxide, sodium hydroxide, potassium hydroxide, calcium hydroxide, sodium carbonate, potassium carbonate, sodium bicarbonate, and potassium bicarbonate.

Examples of the organic base include pyridine, triethylamine, and ethyldiisopropylamine.

The base may be used alone or in combination of two or more kinds thereof. In a case where two or more kinds thereof are used in combination, the combination and the ratio between the bases can be selected as appropriate depending on the purpose thereof.

The amount of the base to be used is not particularly limited, but is preferably in a range of 1 to 6 times moles and more preferably in a range of 1 to 4 times moles with respect to the amount of the compound (1b) to be used (in the case of the method 2, the total amount of the compound ($1b^1$) and the compound ($1b^2$) to be used).

The reaction during the process of producing the compound ($1^\circ$) according to the method 1 and the method 2 may be performed using a catalyst.

The catalyst is not particularly limited and can be selected as appropriate depending on the purpose thereof, and preferred examples thereof include 4-dimethylaminopyridine (DMAP).

The catalyst may be used alone or in combination of two or more kinds thereof. In a case where two or more kinds thereof are used in combination, the combination and the ratio between the catalysts can be selected as appropriate depending on the purpose thereof, but it is usually sufficient to use only one type of catalyst.

The amount of the catalyst to be used is not particularly limited, but is preferably in a range of 0.01 to 0.3 times moles and more preferably in a range of 0.01 to 0.1 times moles with respect to the amount of the compound (1b) to be used (in the case of the method 2, the total amount of the compound ($1b^1$) and the compound ($1b^2$) to be used).

It is preferable that the conditions for the reaction during the process of producing the compound ($1^\circ$) according to the method 1 and the method 2 are adjusted as appropriate so that the reaction satisfactorily proceeds. In this case, the reaction temperature is typically preferably in a range of 15° C. to 80° C. and more preferably in a range of 20° C. to 60° C. Further, the reaction time is preferably in a range of 0.5 to 36 hours and more preferably in a range of 0.5 to 24 hours.

In the process of producing the compound ($1^\circ$) according to the method 1 and the method 2, the target compound ($1^\circ$) can be extracted using a known technique by performing a post-treatment using a known technique as necessary after the reaction is completed. In other words, the compound ($1^\circ$) can be extracted by performing any one or two or more of post-treatments such as filtration, washing, extraction, pH adjustment, dehydration, and concentration as necessary after the reaction is completed and then performing concentration, crystallization, re-precipitation, and column chromatography. Further, the extracted compound ($1^\circ$) may be purified by performing any one or two or more of operations such as crystallization, re-precipitation, column chromatography, extraction, and stirring and washing of crystals using a solvent as necessary one or more times.

The compound ($1^\circ$) is subjected to the post-treatment as necessary after the reaction is completed and then may be subsequently used for intended applications without being extracted.

The compound ($1^\circ$) may be easily obtained by being placed under acidic conditions during the process immediately before extraction of a reaction product to be obtained or immediately before use for intended applications.

The structure of the obtained compound ($1^\circ$) can be confirmed using known techniques such as nuclear magnetic resonance (NMR) spectrometry, mass spectrometry (MS), infrared spectroscopy (IR), and ultraviolet-visible spectroscopy (UV-VIS absorption spectrum).

As the compound (1a) and the compound (1b), commercially available products may be used or compounds produced using known methods may be used.

For example, the compound (1a) is obtained by reacting a compound, in which both of $R^1$ and $R^2$ in the compound (1) are substituted with a hydrogen atom, with a hydroxide formed from M and a hydroxide ion. After the reaction is completed, the compound (1a) is used in the process of producing the compound ($1^\circ$), by extracting the compound (1a) according to the same method as the method used for the compound ($1^o$), or without extracting the compound (1a), using it in a state of a solution or a dispersion liquid.

According to the production method described above, two or more compounds ($1^o$) can be produced during the reaction. Therefore, in a case where a mixture of these compounds ($1^o$) is produced during the reaction, the target compound ($1^o$) can be separated therefrom by applying the above-described purification method one or more times as necessary.

According to the production method described above, the production rates of any of the two or more compounds ($1^o$) can be improved by adjusting the reaction conditions.

Between two hydroxyl groups in the target compound (1a) for the reaction, a hydroxyl group present in the terminal of a molecule has higher reactivity in the present process than that of a hydroxyl group bonded to a carbon atom adjacent to a carbonyl group. Accordingly, typically, the compound ($1^{o1}$)-3 and the compound ($1^{o2}$)-3 are the most likely to be produced, the compound ($1^{o1}$)-2 and the compound ($1^{o2}$)-2 are less likely to be produced, and the compound ($1^{o1}$)-1, the compound ($1^{o2}$)-1, the compound ($1^{o3}$)-1, and the compound ($1^{o3}$)-2 are least likely to be produced under the same reaction conditions. Accordingly, the yield of the target compound ($1^o$) can be improved by adjusting the reaction conditions in consideration of the difference in reactivity.

For example, in the case of the method 1, the production rate and the yield of the compound ($1^{o1}$)-1 can be improved by increasing the amount of the compound (1b) to be used, by setting the amount of the compound (1b) to be used with respect to the amount of hydroxyl groups in the compound (1a) to be preferably in a range of 2 to 6 times moles and more preferably in a range of 3 to 5 times moles.

Further, in the case of the method 1, the production rates and the yields of the compound ($1^{o1}$)-2 and the compound ($1^{o1}$)-3 can be improved by decreasing the amount of the compound (1b) to be used, by setting the amount of the compound (1b) to be used with respect to the amount of hydroxyl groups in the compound (1a) to be preferably in a range of 1 to 3 times moles and more preferably in a range of 1.5 to 2.5 times moles.

Even in the case of the method 2, similarly, the production rate and the yield of the specific compound ($1^o$) can be improved by adjusting the amount of the compound (1b) to be used (the total amount of the compound ($1b^1$) and the compound ($1b^2$) to be used) or adjusting the ratio between the amounts of the compound ($1b^1$) and the compound ($1b^2$) to be used.

<Method of Producing Salt of Compound>

For example, the salt of the compound (1) can be produced by treating the reaction product immediately before extraction with an excessive amount of acid or base in the method of producing the compound (1) (compound)($1^o$) described above.

Further, the salt of the compound (1) can be also produced by treating the extracted compound (1) (compound)($1^o$) with an excessive amount of acid or base.

In both cases, the salt of the compound (1) can be extracted using the same method as the method used for the compound (1).

<External Agent for Skin and Cosmetic>

The external agent for skin according to the present invention contains the compound (1) or a salt thereof.

Since the compound (1) and the like have excellent affinity for skin and percutaneous absorbability, the external agent for skin has excellent permeability into the skin. Therefore, the external agent for skin is highly effective in ameliorating symptoms caused by the deficiency of pantothenic acid and is useful as active components of a sebum control agent, a normalizing agent for skin turnover, an anti-inflammatory agent, an anti-acne agent, a skin roughness-preventing agent, a hair whitening-preventing agent, an external agent for hair growth, an anti-aging agent, and the like.

In addition, the cosmetic according to the present invention contains the external agent for skin. In other words, the external agent for skin can be used as a cosmetic.

Examples of the types of the external agent for skin and the cosmetic include cosmetics for hair such as shampoos, oil shampoos, cream shampoos, conditioning shampoos, shampoos for dandruffs, shampoos for hair color, rinse-integrated shampoos, rinses, treatments, hair packs, hair foam, hair mousse, hair sprays, hair mists, hair waxes, hair gels, water grease, setting lotions, color lotions, hair tonics, hair liquids, pomade, stick pomade, hair creams, hair brows, split end menders, hair oils, permanent wave agents, straight permanent treatment agents, oxidizing hair dyes, hair bleaches, hair color pre-treatments, hair color post-treatments, permanent pre-treatments, permanent post-treatments, hair manicures, and hair growth agents; basic cosmetics such as face washes, cleansing foams, wash powders, face wash powders, cleansing creams, cleansing milks, cleansing lotions, cleansing gels, cleansing oils, cleansing masks, toners, soft toners, astringent toners, cleansing toners, multilayer toners, emulsions, emollient lotions, moisture lotions, milky lotions, nourishing lotions, nourishing milks, skin moistures, moisture emulsions, massage lotions, cleansing lotions, protect emulsions, sun protects, sun protectors, UV care milks, sunscreens, makeup lotions, horny smoothers, elbow lotions, hand lotions, body lotions, creams, emollient creams, nutritive creams, nourishing creams, vanishing creams, moisture creams, night creams, massage creams, cleansing creams, makeup creams, base creams, pre-makeup creams, sunscreen creams, suntan creams, hair-removal creams, deodorant creams, shaving creams, horny softening creams, gels, cleansing gels, moisture gels, soaps, toilet soaps, transparent soaps, medicated soaps, liquid soaps, shaving soaps, synthetic toilet soaps, packs, masks, peel-off packs, powder packs, washing packs, oil packs, cleansing packs, essences, moisturizing essences, whitening essences, UV protection essences, liposome essences, and liposome toners; makeup cosmetics such as white powder and dusting powder, foundations, makeup bases, lipsticks, lip glosses, blushers, eyeliners, mascaras, eye shadows, eyebrow pencils, eyebrows, nail enamels, enamel removers, and nail treatments; fragrance cosmetics such as fragrances, perfumes, parfums, eau de parfums, eau de toilette, eau de colognes, solid perfumes, aroma powders, perfume soaps, body lotions, and bath oils; body cosmetics such as body shampoos, body cleansers, body powders, deodorant lotions, deodorant powders, deodorant sprays, deodorant sticks, deodorant cosmetics, decoloring agents, depilatories, bath preparations, insect repellent sprays, and insect repellers; ointments, patches, lotions, liniments, and liquid coating agents.

Examples of the dosage forms of the external agent for skin and the cosmetic include emulsion types such as oil-in-water (O/W) type, a water-in-oil (W/O) type, a W/O/W type, and an O/W/O type; an emulsified polymer type; an oil type; a solid type; a liquid type; a kneaded type; a stick type; a volatile oil type; a powder type; a jelly type;

a gel type; a paste type; a cream type; a sheet type; a film type; a mist type; a spray type; a multilayer type; a foam type; and a flake type.

The external agent for skin and the cosmetic are not limited as long as the external agent for skin and the cosmetic contain one or more selected from the group consisting of the compound (1) and a salt thereof as indispensable components. Further, the external agent for skin and the cosmetic which contain the compound (1) and do not contain the salt of the compound (1), contain the salt of the compound (1) and do not contain the compound (1), or contain both of the compound (1) and the salt of the compound (1) may be used.

The type of compound (1) contained in the external agent for skin may be only one or two or more. In a case where two or more types of compounds are used, the combination and the ratio between the compounds can be selected as appropriate depending on the purpose thereof.

Similarly, the salt of the compound (1) contained in the external agent for skin may be only one or two or more. In a case where two or more types of salts are used, the combination and the ratio between the salts can be selected as appropriate depending on the purpose thereof.

The external agent for skin and the cosmetic may contain raw ingredients, described in existing raw ingredient specifications or public documents, at a typical concentration of 100 ppm to 90% by mass with respect to the total amount of the external agent for skin or the cosmetic. Examples of the raw ingredients include those described in the Japanese Pharmacopoeia Fourteenth Edition (edited by Pharmaceutical and Medical Device Regulatory Science Society of Japan, published by Jiho, Inc., April, 2001); Japanese Standards of Cosmetic Ingredients second edition commentary, (edited by Pharmaceutical and Medical Device Regulatory Science Society of Japan, published by YAKUJI NIPPO LTD., 1984); The Japanese Cosmetic Ingredients Codex (supervised by Pharmaceutical Affairs Bureau, Evaluation Division, published by YAKUJI NIPPO, LTD., 1993); Supplement To The Japanese Cosmetic Ingredients Codex (supervised by Pharmaceutical Affairs Bureau, Evaluation Division, published by YAKUJI NIPPO, LTD., 1993); The Comprehensive Licensing Standards of Cosmetics by Category (supervised by Pharmaceutical Affairs Bureau, Evaluation Division, published by YAKUJI NIPPO, LTD., 1993); International Cosmetic Ingredient Dictionary and Handbook 2002 Ninth Edition Vol. 1 to 4, by CTFA; and Cosmetic Ingredients Dictionary (published by Nikko Chemicals Co., Ltd, 1991).

In addition to the indispensable components described above, the external agent for skin may contain components typically used for external agents for skin, for example, carriers which are pharmaceutically acceptable as external agent for skin and additives as necessary within a range that does not impair the effects of the present invention.

Examples of such components include water and hydrocarbons, natural fats and oils, fatty acids, higher alcohols, alkyl glyceryl ethers, esters, silicone oils, polyhydric alcohols, monovalent lower alcohols, saccharides, polymers, anionic surfactants, cationic surfactants, amphoteric surfactants, non-ionic surfactants, natural surfactants, ultraviolet absorbing agents, powders, coloring materials, amino acids, peptides, vitamins, vitamin-like active factors, preservatives, antioxidants, sequestering agents, humectants, anti-inflammatory agents, pH regulators, salts, organic acids, whitening agents, essential oils, terpenes, and perfumes, described in paragraphs [0018] to [0050] of Japanese Unexamined Patent Application, First Publication No. 2012-236800.

The pharmaceutically acceptable carriers may be used alone or in combination of two or more kinds thereof. In a case where two or more kinds thereof are used in combination, the combination and the ratio between the carriers can be selected as appropriate depending on the purpose thereof.

The cosmetic of the present invention may contain optional components known in the art according to a conventional method in addition to the above-described components exemplified as the components contained in the external agent for skin.

The optional components are not particularly limited and can be selected as appropriate depending on the purpose thereof.

The optional components may be used alone or in combination of two or more kinds thereof. In a case where two or more kinds thereof are used in combination, the combination and the ratio between the components can be selected as appropriate depending on the purpose thereof.

The content of the optional components contained in the cosmetic is not particularly limited and may be adjusted depending on the purpose thereof.

In the external agent for skin and the cosmetic according to the present invention, the total content of the compound (1) and a salt thereof (the content of indispensable components) is preferably in a range of 0.01% to 20% by mass, more preferably in a range of 0.05% to 12% by mass, and particularly preferably in a range of 0.1% to 10% by mass. When the total content of the compound (1) and a salt thereof is greater than or equal to the lower limit described above, the compound (1) and a salt thereof are rapidly transferred to the skin and more excellent effects as an external agent or a cosmetic can be obtained. Further, when the total content of the compound (1) and a salt thereof is less than or equal to the upper limit described above, overuse of these components is prevented.

The dose of the external agent for skin according to the present invention cannot be unconditionally determined because the dose thereof varies depending on the symptoms, the weight, the age, the gender, and the like of a patient, but it is preferable that the dose (total dose of the compound (1) and a salt thereof) of the external agent for skin is typically set such that the dose of active components is in a range of 0.4 to 400 mg/person for an adult per day.

The external agent for skin is administered by dividing a predetermined amount into one dose or multiple doses per day.

The amount of the cosmetic to be used according to the present invention cannot be unconditionally determined because the amount thereof to be used varies depending on the symptoms, the weight, the age, the gender, and the like of a patient, but it is preferable that the amount (total amount of the compound (1) and a salt thereof to be used) of the cosmetic to be used is typically set such that the amount of active components to be used is in a range of 0.4 to 400 mg/person for an adult per day.

The cosmetic is also administered by dividing a predetermined amount into one dose or multiple doses per day.

The compound (1) and a salt thereof are excellently effective in ameliorating symptoms caused by the deficiency of pantothenic acid as described above. Therefore, the dose of the active components when the external agent for skin according to the present invention is used can be reduced compared to the dose of the active components in an external agent for skin of the related art which ameliorate the symptoms caused by the deficiency of pantothenic acid.

Similarly, the amount of the active components to be used when the cosmetic according to the present invention is used can also be reduced compared to the amount of the active components to be used in a cosmetic of the related art which ameliorate the symptoms caused by the deficiency of pantothenic acid.

The external agent for skin and the cosmetic can be produced by blending components required for configuring a target object, for example, the compound (1) or a salt thereof and other components (pharmaceutically acceptable carriers and other components) as necessary for formulation.

The external agent for skin and the cosmetic can be produced using the same method as the method used for known external agents for skin and cosmetics except that the components to be blended are different.

<Food Additive>

A food additive of the present invention contains the compound (1) or a salt thereof.

Since the compound (1) and the like have high absorbability into a body, the food additive is excellently effective in ameliorating symptoms caused by the deficiency of pantothenic acid similar to the case of the external agent for skin and the cosmetic.

Similar to the dosage forms of known food additives, examples of the dosage forms of the food additive include a tablet, a coated tablet, a pill, powder, a granule, a capsule, a liquid, a suspension, and an emulsion.

Similar to the case of the external agent for skin and the cosmetic, the food additive is not limited as long as the food additive contains one or more selected from the group consisting of the compound (1) and a salt thereof as indispensable components. Further, the food additive which contains the compound (1) and does not contain the salt of the compound (1), contains the salt of the compound (1) and does not contain the compound (1), or contains both of the compound (1) and the salt of the compound (1) may be used.

The type of compound (1) contained in the food additive may be only one or two or more. In a case where two or more types of compounds are used, the combination and the ratio between the compounds can be selected as appropriate depending on the purpose thereof.

Similarly, the salt of the compound (1) contained in the food additive may be only one or two or more. In a case where two or more types of salts are used, the combination and the ratio between the salts can be selected as appropriate depending on the purpose thereof.

The food additive may contain optional components known in the art according to a conventional method in addition to the above-described indispensable components.

The optional components are not particularly limited and can be selected as appropriate depending on the purpose thereof.

The optional components may be used alone or in combination of two or more kinds thereof. In a case where two or more kinds thereof are used in combination, the combination and the ratio between the components can be selected as appropriate depending on the purpose thereof.

The content of the optional components contained in the food additive is not particularly limited and may be adjusted depending on the purpose thereof.

The total content of the compound (1) and a salt thereof (the content of indispensable components) contained in the food additive is not particularly limited and may be adjusted as appropriate depending on the purpose thereof, but is typically preferably in a range of 0.001% to 0.1% by mass.

The amount of the food additive according to the present invention cannot be unconditionally determined because the amount thereof varies depending on the purpose thereof, but it is preferable that the amount (total intake of the compound (1) and a salt thereof) of the food additive to be used is typically set such that the intake of active components is in a range of 10 to 1000 mg/person for an adult per day.

The food additive can be produced using the same method as the method used for known food additives except that the components to be blended are different.

EXAMPLES

Hereinafter, the present invention will be described in more detail with reference to specific examples. However, the present invention is not limited to the examples described below. Further, hereinafter, the unit "M" of the concentration indicates "mol/L" and the unit "mM" indicates "mmol/L".

In examples and reference examples described below, a target object was quantified using HPLC analysis under following conditions (analysis conditions 1).

(HPLC Analysis Conditions 1)

Column: Two of "Shodex (registered trademark) Silica 5C8 4E (4.6 mm I.D.×250 mm)" (manufactured by Showa Denko K.K.) were connected to each other and then used.

Eluent: $H_3PO_4$, $KH_2PO_4$ aqueous solution (concentration of $H_3PO_4$: 15 mM, concentration of $KH_2PO_4$: 15 mM)/acetonitrile=30/70 (volume ratio)

Flow rate: 1.2 mL/min

Column temperature: 40° C.

Detector: UV (wavelength of 210 nm) and RI

Sample injection volume: 20 µL

In the examples and the reference examples described below, a target object was identified by measuring NMR. The measurement of NMR was performed using a solution obtained by dissolving approximately 20 mg of a sample to be measured in approximately 600 mg of deuterated chloroform ($CDCl_3$) and "Avance-500" (manufactured by Bruker Biospin Corp.) as a measuring device.

In Comparative Example 1 described below, sodium pantothenate was quantified using HPLC analysis under following conditions (analysis conditions 2).

(HPLC Analysis Conditions 2)

Column: Two of "Shodex (registered trademark) Rspak (trademark) NN-814 (8.0 mm I.D.×250 mm)" (manufactured by Showa Denko K.K.) were connected to each other and then used.

Eluent: 0.1 M $H_3PO_4$ aqueous solution

Flow rate: 1.0 mL/min

Column temperature: 40° C.

Detector: UV (wavelength of 210 nm) and RI

Sample injection volume: 20 µL

<Production of Compound>

Example 1

A compound (compound in which $R^1$ represents a hydrogen atom and $R^2$ represents a linear hexadecanoyl group in Formula (1), hereinafter, also simply referred to as a "compound (1)-301") represented by Formula (1)-301 was produced according to the following procedures.

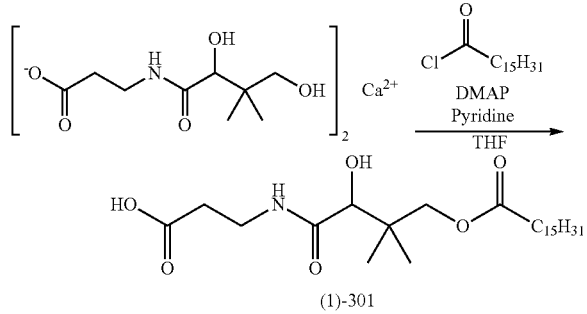

(1)-301

Calcium pantothenate (manufactured by Tokyo Kasei Kogyo Co., Ltd., 19.1 g, 40.1 mmol), pyridine (manufactured by Wako Pure Chemical Industries, Ltd., 19.0 g, 240 mmol), and 4-dimethylaminopyridine (DMAP) (manufactured by Wako Pure Chemical Industries, Ltd., 0.49 g, 4.0 mmol) were added to tetrahydrofuran (THF) (manufactured by Wako Pure Chemical Industries, Ltd., 560 mL) and stirred, palmitoyl chloride (manufactured by Tokyo Kasei Kogyo Co., Ltd., 22.6 g, 82.2 mmol) was added dropwise, as an acylating agent, to the obtained white suspension at room temperature (25° C.) for 3 hours, and the solution was further stirred at room temperature for 3.5 hours after the dropwise addition. When the reaction solution was partially sampled at this time point, analyzed using HPLC, and quantified, the yield of a target compound (1)-301 was 20.7%.

The reaction was stopped by adding water (100 mL) to the reaction solution, THF was distilled off through concentration under reduced pressure, the concentrate was transferred to a separatory funnel, and dichloromethane (manufactured by Wako Pure Chemical Industries, Ltd., 400 mL) was added thereto. As the result, the water layer was emulsified. The emulsion was eliminated by adding 2N hydrochloric acid thereto and adjusting the pH of the water layer to 3. Next, the organic layer was washed with 0.01 N hydrochloric acid (400 mL) two times and water (200 mL) two times in this order. The organic layer was dried over anhydrous sodium sulfate, dichloromethane was distilled off through concentration under reduced pressure, and the organic layer was dried in vacuum, thereby obtaining a white solid (32.3 g) which is a crude product.

The obtained crude product was purified using column chromatography (silica gel, hexane:ethyl acetate=6:4 (volume ratio)), and then the target compound (1)-301 (IUPAC name: 3-[N-(4-hexadecanoyloxy-3,3-dimethyl-2-hydroxybutyryl)amino]propionic acid) was obtained as a white solid (yield of 3.47 g (7.59 mmol), isolated yield of 9.5%).

It was confirmed that the obtained product was the compound (1)-301 from $^1$H-NMR and $^{13}$C-NMR analysis, and the purity of the compound (1)-301 was specified as 96% according to an area percentage method based on HPLC analysis (RI detector) data.

The NMR data of the obtained compound (1)-301 is as follows.

$^1$H-NMR (500 MHz, CDCl$_3$): δ (ppm)=7.25 (br t, J=6.3 Hz, 1H, NH), 4.19 (d, J=11.0 Hz, 1H, AcylOCH$_2$), 3.89 (s, 1H, CH), 3.78 (d, J=11.0 Hz, 1H, AcylOCH$_2$), 3.56 (m, 2H, NHCH$_2$), 2.60 (m, 2H, CH$_2$CO$_2$H), 2.34 (t, J=7.5 Hz, 2H, COCH$_2$), 1.62 (m, 2H, COCH$_2$CH$_2$), 1.30-1.24 (m, 24H, (CH$_2$)$_{12}$), 1.05 (s, 3H, C(CH$_3$)$_2$), 0.94 (s, 3H, C(CH$_3$)$_2$), 0.88 (t, J=6.8 Hz, 3H, CH$_2$CH$_3$)

$^{13}$C-NMR (125 MHz, CDCl$_3$): δ (ppm)=176.0 (COOH), 174.8, 172.7 (C=O), 75.0 (CHO), 70.3 (CH$_2$O), 38.7 (C(CH$_3$)$_2$), 34.7, 34.4, 33.9, 31.9, 29.7, 29.7, 29.6, 29.5, 29.4, 29.3, 29.2, 25.0, 22.7 (CH$_2$), 21.4, 19.8 (C(CH$_3$)$_2$), 14.1 (CH$_2$CH$_3$)

Example 2

A compound (compound in which R$^1$ represents a hydrogen atom and R$^2$ represents a branched 2-hexyldecanoyl group in Formula (1), hereinafter, also simply referred to as a "compound (1)-302") represented by Formula (1)-302 was produced according to the following procedures.

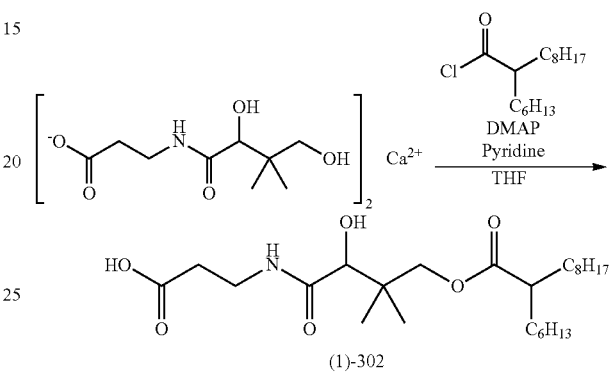

(1)-302

The reaction was performed in the same manner as in Example 1 except that 2-hexyldecanoyl chloride (manufactured by Nippon Fine Chemical Co., Ltd.) was used as an acylating agent in place of palmitoyl chloride and the reaction temperature was set to 50° C. in place of room temperature. When the reaction solution was partially sampled, analyzed using HPLC, and quantified, the yield of a target compound (1)-302 was 13.4%. Hereinafter, the target compound (1)-302 (IUPAC name: 3-[N-(4-(2-hexyldecanoyl)oxy-3,3-dimethyl-2-hydroxybutyryl)amino]propionic acid) was obtained as a pale yellow oil (yield of 2.74 g (5.99 mmol), isolated yield of 7.5%) by performing the post-treatment of the reaction solution, extraction of the crude product, and purification using column chromatography according to the same method as in Example 1.

It was confirmed that the obtained product was the compound (1)-302 from $^1$H-NMR and $^{13}$C-NMR analysis, and the purity of the compound (1)-302 was specified as 98% according to an area percentage method based on HPLC analysis (RI detector) data.

The NMR data of the obtained compound (1)-302 is as follows.

$^1$H-NMR (500 MHz, CDCl$_3$): δ (ppm)=7.32 (br t, J=6.3 Hz, 1H, NH), 4.19 (d, J=11.0 Hz, 1H, AcylOCH$_2$), 3.89 (s, 1H, CH), 3.79 (d, J=11.0 Hz, 1H, AcylOCH$_2$), 3.55 (m, 2H, NHCH$_2$), 2.60 (m, 2H, CH$_2$CO$_2$H), 2.36 (m, 1H, COCH), 1.59 (m, 2H, COCH(CH$_2$)$_2$), 1.46 (m, 2H, COCH(CH$_2$)$_2$), 1.31-1.22 (m, 20H, CH$_2$), 1.06 (s, 3H, C(CH$_3$)$_2$), 0.94 (s, 3H, C(CH$_3$)$_2$), 0.87 (m, 6H, CH$_2$CH$_3$)

$^{13}$C-NMR (125 MHz, CDCl$_3$): δ (ppm)=177.5 (COOH), 175.9, 172.8 (C=O), 75.3 (CHO), 70.4 (CH$_2$O), 45.9 (COCH), 38.7 (C(CH$_3$)$_2$), 34.7, 33.9, 32.3, 32.3, 31.9, 31.7, 29.6, 29.4, 29.3, 29.2, 27.5, 27.4, 22.7, 22.6 (CH$_2$), 21.4, 19.7 (C(CH$_3$)$_2$), 14.1, 14.1 (CH$_2$CH$_3$)

Reference Example 1

A compound (hereinafter, also simply referred to as a "compound (9)-101") represented by Formula (9)-101 was produced according to the following procedures.

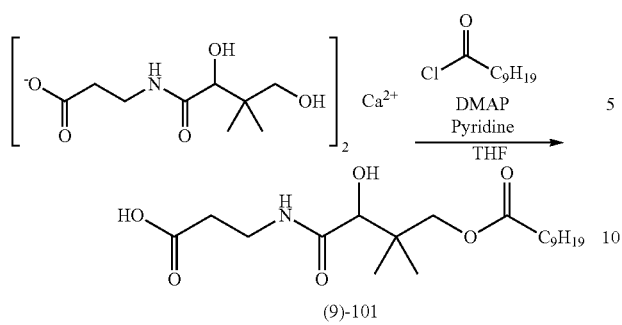

(9)-101

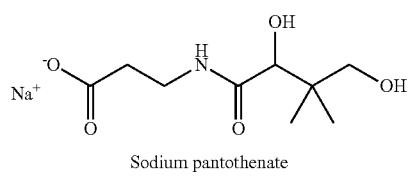

Sodium pantothenate

The reaction was performed in the same manner as in Example 1 except that decanoyl chloride (manufactured by Tokyo Kasei Kogyo Co., Ltd.) was used as an acylating agent in place of palmitoyl chloride. When the reaction solution was partially sampled, analyzed using HPLC, and quantified, the yield of a target compound (9)-101 was 24.4%. Hereinafter, the target compound (9)-101 (IUPAC name: 3-[N-(4-decanoyloxy-3,3-dimethyl-2-hydroxybutyryl)amino]propionic acid) was obtained as a white solid (yield of 3.41 g (9.14 mmol), isolated yield of 11.4%) by performing the post-treatment of the reaction solution, extraction of the crude product, and purification using column chromatography according to the same method as in Example 1.

It was confirmed that the obtained product was the compound (9)-101 from $^1$H-NMR and $^{13}$C-NMR analysis, and the purity of the compound (9)-101 was specified as 98% according to an area percentage method based on HPLC analysis (RI detector) data.

The NMR data of the obtained compound (9)-101 is as follows.

$^1$H-NMR (500 MHz, CDCl$_3$): δ (ppm)=7.25 (br t, J=6.3 Hz, 1H, NH), 4.19 (d, J=11.0 Hz, 1H, AcylOCH$_2$), 3.89 (s, 1H, CH), 3.78 (d, J=11.0 Hz, 1H, AcylOCH$_2$), 3.56 (m, 2H, NHCH$_2$), 2.60 (m, 2H, CH$_2$CO$_2$H), 2.33 (t, J=7.5 Hz, 2H, COCH$_2$), 1.61 (m, 2H, COCH$_2$CH$_2$), 1.32-1.22 (m, 12H, (CH$_2$)$_6$), 1.04 (s, 3H, C(CH$_3$)$_2$), 0.95 (s, 3H, C(CH$_3$)$_2$), 0.89 (t, J=6.8 Hz, 3H, CH$_2$CH$_3$)

$^{13}$C-NMR (125 MHz, CDCl$_3$): δ (ppm)=176.2 (COOH), 174.9, 172.5 (C=O), 75.2 (CHO), 70.1 (CH$_2$O), 38.7 (C(CH$_3$)$_2$), 34.7, 34.4, 33.9, 31.9, 29.7, 29.6, 29.5, 29.2, 25.0, 22.7 (CH$_2$), 21.4, 19.9 (C(CH$_3$)$_2$), 14.2 (CH$_2$CH$_3$)

<Skin Permeability Test>

The compound (1)-301, the compound (1)-302, the compound (9)-101, and sodium pantothenate (manufactured by Tokyo Kasei Kogyo Co., Ltd., the compound represented by the following formula) were respectively dissolved in Dubecco's PBS (−), and the pH of a solution was adjusted to 7.4 using a sodium hydroxide aqueous solution or hydrochloric acid, to obtain a solution having a concentration of 0.2% by mass as a sample solution.

A three-dimensionally cultured human skin model ("EPI-606X", manufactured by KURABO INDUSTRIES LTD.) was set such that the lower portion thereof was immersed in a 6-well plate containing the PBS solution (1 mL), and was allowed to stand in an incubator for 30 minutes under conditions of 37° C. at a carbon dioxide concentration of 5%. Next, the PBS solution was replaced with an HBSS (−) solution (1 mL) (hereinafter, referred to as a "receiver liquid"), the sample solution (700 μL) obtained in the above-described manner was added to the skin model, and the skin model was allowed to stand in an incubator under conditions of 37° C. at a carbon dioxide concentration of 5%.

After the skin model was allowed to stand for 24 hours, the sample solution on the skin model was removed using a pipette, the skin model was taken out from the well and washed with the PBS (−) solution. Subsequently, a slice was cut from the skin model and put into a 2 mL tube. Methanol (1 mL) and stainless steel beads (manufactured by Tomy Company, Ltd., diameter of 5.5 mm) were added to the tube, and the slice was crushed under conditions of 2000 rpm for 10 seconds ten times using MULTI BEADS SHOCKER (manufactured by Yasui Kikai Corporation).

After the slice was crushed, the obtained solution was transferred to a 2 mL Eppendorf tube and centrifuged at 12000 rpm for 5 minutes, the supernatant was filtered using a filter (pore size of 0.22 μm), thereby obtaining a skin model extract.

Next, the compound (1)-301, the compound (1)-302, the compound (9)-101, and sodium pantothenate in the skin model extract and the receiver liquid were quantified by analyzing each of the compounds (test substances) using HPLC described above, and a total value A (μg) of these quantitative values was calculated. Further, the permeability into the skin model (%) of each of the compound (1)-301 (Example 1), the compound (1)-302 (Example 2), the compound (9)-101 (Reference Example 1), and sodium pantothenate (Comparative Example 1) added to the skin model was calculated according to Equation (i). The results thereof are listed in Table 1.

$$\text{Permeability (\%)} = (A/1400) \times 100 \qquad (i)$$

TABLE 1

| | Test compound | Permeability (%) |
|---|---|---|
| Example 1 | Compound (1)-301 (R$^1$: H, R$^2$: —C(=O)—C$_{15}$H$_{31}$) | 41 ± 4.7 |
| Example 2 | Compound (1)-302 (R$^1$: H, R$^2$: —C(=O)—C$_9$H$_{18}$(C$_6$H$_{13}$)) | 44 ± 2.7 |
| Reference Example 1 | Compound (9)-101 (R$^1$: H, R$^2$: —C(=O)—C$_9$H$_{19}$) | 29 ± 0.8 |
| Comparative Example 1 | Sodium pantothenate | 18 ± 0.4 |

As evident from the results described above, even among pantothenic acid derivatives, the compound (1)-302, the compound (1)-301, and the compound (9)-101, in which hydroxyl groups were acylated, had clearly higher permeability than the permeability of sodium pantothenate having two hydroxyl groups as they were. Further, the compound (1)-302 and the compound (1)-301, in which the number of carbon atoms in an acyl group (R$^2$) was higher, had clearly higher permeability than the permeability of the compound (9)-101, even though they are the same in that hydroxyl groups were acylated. The permeability of the compound (1)-302 and the permeability of the compound (1)-301 were almost the same as each other, and the presence of a branched chain in an acyl group of the compound (1) had little effect on the permeability.

As described above, it was shown that, even among pantothenic acid derivatives, the compound of the present invention has a remarkably high permeability and is extremely excellent as an active component of an external agent for skin.

INDUSTRIAL APPLICABILITY

The present invention can be applied to external agents for skin, cosmetics, and food additives.

The invention claimed is:

1. A compound of Formula (1) or a salt thereof,

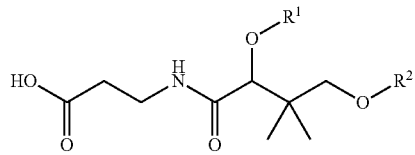
(1)

(in the formula, $R^1$ and $R^2$ each independently is a hydrogen atom or a linear or branched acyl group having 11 to 18 carbon atoms, a hydrocarbon group bonded to a carbonyl carbon of the acyl group is a saturated or unsaturated hydrocarbon group, and at least one of $R^1$ and $R^2$ is the acyl group).

2. The compound or a salt thereof according to claim 1, wherein the compound of Formula (1) is a compound of Formula (1)-3,

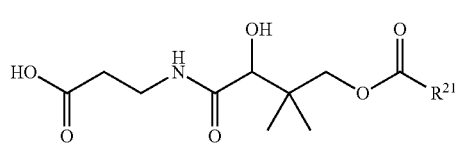
(1)-3

(in the formula, $R^{21}$ is a linear or branched saturated or unsaturated hydrocarbon group having 10 to 17 carbon atoms).

3. The compound or a salt thereof according to claim 1, wherein $R^1$ and $R^2$ each independently is a hydrogen atom or a linear or branched acyl group having 14 to 18 carbon atoms.

4. The compound or a salt thereof according to claim 2, wherein $R^{21}$ is a linear or branched saturated or unsaturated hydrocarbon group having 15 to 17 carbon atoms.

5. The compound or a salt thereof according to claim 1, wherein the compound of Formula (1) is a compound of Formula (1)-301 or (1)-302

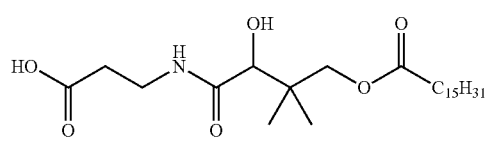
(1)-301

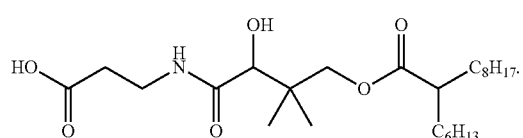
(1)-302

6. The compound or a salt thereof according to claim 1, wherein the salt of the compound is a salt formed by the compound becoming a cation together with an inorganic anion or an organic anion or a salt formed by the compound becoming an anion together with an inorganic cation or an organic cation.

7. The compound or a salt according to claim 1, wherein the salt of the compound is a salt formed by the compound becoming a cation together with one or more anions selected from the group consisting of a hydroxide ion, a nitrate ion, a sulfate ion, a carbonate ion, a bicarbonate ion, a halide ion, a formate ion, an acetate ion, a citrate ion, a tartrate ion, an oxalate ion, a fumarate ion, anions of saturated or unsaturated chain fatty acid having 3 to 20 carbon atoms, anions of carnitine and derivatives thereof, anions of hydroxy citric acid and derivatives thereof, anions of ascorbic acid, and anions of ascorbyl phosphoric acid and derivatives thereof.

8. The compound or a salt thereof according to claim 1, wherein the salt of the compound is a salt formed by the compound becoming an anion together with one or more cations selected from the group consisting of a sodium ion, a potassium ion, a calcium ion, a magnesium ion, a zinc ion, an ammonium ion, carnitine, and cations of carnitine derivatives.

9. An external agent for skin comprising: the compound or a salt thereof according to claim 1.

10. A cosmetic comprising: the external agent for skin according to claim 9.

11. A food additive comprising: the compound or a salt thereof according to claim 1.

12. The compound or a salt thereof according to claim 1, wherein $R^1$ and $R^2$ each independently is a hydrogen atom or a linear or branched acyl group having 11 to 18 carbon atoms, a hydrocarbon group bonded to a carbonyl carbon of the acyl group is a saturated hydrocarbon group, and at least one of $R^1$ and $R^2$ is the acyl group.

* * * * *